United States Patent
Hasson et al.

(10) Patent No.: US 9,999,643 B2
(45) Date of Patent: Jun. 19, 2018

(54) THERAPEUTIC COMPOSITION FOR TREATING GANGRENE

(71) Applicant: SULTAN QABOOS UNIVERSITY, Al-Khodh (OM)

(72) Inventors: Sidgi Syed Anwer Abdo Hasson, Al-Khodh (OM); Ali A. H. Al-Jabri, Al-Khodh (OM)

(73) Assignee: SULTAN QABOOS UNIVERISTY, Al-Khodh (OM)

( * ) Notice: Subject to any disclaimer, the term of this patent is extended or adjusted under 35 U.S.C. 154(b) by 0 days. days.

(21) Appl. No.: 15/785,267

(22) Filed: Oct. 16, 2017

(65) Prior Publication Data
US 2018/0104295 A1 Apr. 19, 2018

Related U.S. Application Data

(60) Provisional application No. 62/410,377, filed on Oct. 19, 2016.

(51) Int. Cl.
*A61K 36/28* (2006.01)
*A61K 36/285* (2006.01)
*A61K 35/20* (2006.01)
*A61K 35/38* (2015.01)

(52) U.S. Cl.
CPC ............. *A61K 36/28* (2013.01); *A61K 35/20* (2013.01); *A61K 35/38* (2013.01)

(58) Field of Classification Search
CPC ...... A61K 36/28; A61K 36/285; A61K 35/20; A61K 35/38
USPC .................................. 424/535, 537
See application file for complete search history.

(56) References Cited

U.S. PATENT DOCUMENTS 9,056,117 B2 * 6/2015 Saxena ................ A61K 36/58

FOREIGN PATENT DOCUMENTS

| CN | 104593177 A | | 5/2015 |
|---|---|---|---|
| CN | 104611163 A | | 5/2015 |
| CN | 105106098 A | | 12/2015 |
| CN | 105250859 A | * | 1/2016 |
| CN | 105878597 A | | 8/2016 |
| CN | 105878605 A | | 8/2016 |
| WO | 2008072256 A1 | | 6/2008 |
| WO | 2008136013 A1 | | 11/2008 |

OTHER PUBLICATIONS

Shweta Chaudhary, et al., In Vitro Thrombolytic Activity of Dhamasa (Fagonia arabica Linn.), Kushta (Saussurea lappa Decne.), and Guduchi (Tinospora cordifolia Thunb.), Ayu 36(4) pp. 421-424 (2015).
Abdalla Ko, An Overview of the Therapeutic Effects of Camel Milk in the Treatment of Type 1 Diabetes Mellitus, Biomolecular Research & Therapeutics 3(3) (2014).
Agrawal RP, Beneficial Effect of Camel Milk in Diabetic Nephropathy, Acta Biomed 80(2) pp. 131-134 (2009).

* cited by examiner

*Primary Examiner* — Chris R Tate
(74) *Attorney, Agent, or Firm* — Richard C. Litman

(57) ABSTRACT

A therapeutic composition for wet and dry gangrene includes an herbal composition alone, or in combination with one or more animal-derived products. The herbal composition can include a mixture of *Saussurea acrophila* Diels, *Saussurea ceratocarpa*, and *Aucklandia lappa* Decne. The mixture can include, for example, a mixture of extracts or whole herbs of *Saussurea acrophila* Diels, *Saussurea ceratocarpa*, and *Aucklandia lappa* Decne. The one or more animal-derived products can include at least one of camel milk and camel saliva.

4 Claims, No Drawings

THERAPEUTIC COMPOSITION FOR TREATING GANGRENE

CROSS-REFERENCE TO RELATED APPLICATION

This application claims the benefit of U.S. Provisional Patent Application Ser. No. 62/410,377, filed Oct. 19, 2016, which is hereby incorporated by reference in its entirety.

BACKGROUND

1. Field

The disclosure of the present patent application relates to medical compositions and treatments, and particularly to a combination therapy using topical and oral administration of an herbal composition of *Saussurea acrophila* Diels, *Saussurea ceratocarpa*, and *Aucklandia lappa* Decne mixed with an animal product for treatment of wet and dry gangrene.

2. Description of the Related Art

Gangrene is a serious condition in which a loss of blood supply causes body tissue to die. It can affect any part of the body but typically starts in the toes, feet, fingers and hands. The management of gangrene differs according to whether it is sterile/aseptic ('dry') or infected/septic ('wet'). In most cases, aseptic dry gangrenous tissue is left to spontaneously detach (auto-amputation). Surgical removal of dead tissues and amputation are usually reserved for infected or septic wet gangrene. However, dry gangrene can develop into wet gangrene, often as a result of infection in immune-compromised patients with diabetes. Therefore, every effort must be made to prevent infection of dry gangrenous tissue.

Elderly, diabetic, and bed-ridden patients with several serious illnesses and patients with a short life expectancy, particularly those in intensive care units, may also require conservative, non-surgical interventions. Moreover, patients may refuse amputations for religious reasons. Some patients are temporarily unable to undergo any surgical intervention, including major amputations. In these cases, transformation of dry to wet gangrene must be prevented, while waiting for improvements in the patient's condition. Apart from loss of man days, cost of treating these non-healing wounds can be tremendous. The prevalence of gangrene of the lower body in the diabetic or elderly patients has been estimated to be 3-11%. The morbidity and mortality associated with this kind of clinical complications is significant. For example, the death rate in patients with pressure ulcers is four fold greater than those without.

Despite efficacious anti-microbial treatment and improved supportive measures, "wet" gangrene treatment still poses immense challenges. Wounds of diabetics are practically unmanageable and are usually regarded as 'incurable'. In fact, diabetes is an important underlying condition in leg ulcers. Various therapies for the treatment of leg ulcers e.g. multi-layer compression-bandage systems, topical recombinant human platelet derived growth factor, human skin equivalent for skin grafting, etc., are available which may aid in wound healing. Quite often, inability to treat wounds leads to amputation of the infected limbs. Wound management in animals poses additional challenges. Unlike humans, chances of exposure of wounds to environmental infestations, in case of animals are much higher.

Thus, a therapy for wet and dry gangrene solving the aforementioned problems is desired.

SUMMARY

A therapeutic composition for wet and dry gangrene includes at least one of an herbal composition and at least one animal product. The herbal composition can include a mixture of an extract or whole herbs of *Saussurea acrophila* Diels, *Saussurea ceratocarpa*, and *Aucklandia lappa* Decne. The extract can be an aqueous or alcohol extract, e.g., ethanolic extract. The at least one animal product can include camel's milk. For example, the camel milk can be harvested from a camel that is fed the herbal composition. The at least one animal product can include a mixture of camel milk and camel saliva.

The therapeutic composition can be used to treat any exposed tissue of a human or animal to alter or improve the nature of the tissue. The therapeutic composition can be used to treat wounds, skin ulcers, necrosis, burns, and/or acute skin properties. The composition can be effective in curing such clinical complications of any nature in humans, especially non-healing wounds of diabetics and wounds referred to as "wet" gangrene.

A method for treating "wet" gangrene, "dry" gangrene, skin ulcer, necrosis and/or acute skin haemorrhage can include administering to a patient in need thereof an effective amount of the therapeutic composition. The therapeutic composition may be administered orally and/or topically.

The composition exhibits remarkable efficacy in treating and curing acute "wet" gangrene, which is generally regarded as 'incurable' in state of the art and mostly requires limb amputation.

These and other features of the present disclosure will become readily apparent upon further review of the following specification and drawings.

DETAILED DESCRIPTION OF THE PREFERRED EMBODIMENTS

A therapeutic composition for wet and dry gangrene includes an herbal composition alone, or in combination with one or more animal-derived products. The herbal composition can include a mixture of *Saussurea acrophila* Diels, *Saussurea ceratocarpa*, and *Aucklandia lappa* Decne. The mixture can include, for example, a mixture of extracts or whole herbs of *Saussurea acrophila* Diels, *Saussurea ceratocarpa*, and *Aucklandia lappa* Decne. The one or more animal-derived products can include at least one of camel milk and camel saliva. The camel milk can be treated to remove any fat included therein.

In an embodiment, the therapeutic composition can include about 4% to about 15% of an extract of *Saussurea acrophila* Diels, about 6% to about 9% of an extract of *Saussurea ceratocarpa*, and about 45% to about 65% of an extract of *Aucklandia lappa* Decne. The extract of *Aucklandia lappa* Decne can be prepared from the root of *Aucklandia lappa* Decne. The extract of *Saussurea acrophila* Diels can be prepared from the stem, leaves, and bark of *Saussurea acrophila* Diels. The extract of *Saussurea ceratocarpa* can be prepared from the stem, leaves, and bark of *Saussurea ceratocarpa*. The composition can be prepared from the above herbal extracts and mixed with a general preservative, e.g., copper sulphate, a thickening agent, e.g., bee wax, decolorizing agents, e.g., activated charcoal, Fuller's earth, Calcium-D-Saccharate, Serolite, Bentonite, or magnesium oxide, coloring agents, fragrances, opacifiers, and/or vitamins.

The therapeutic composition can be administered to a patient for healing of wounds, and specifically, healing of wounds associated with gangrene. The therapeutic composition is capable of treating a variety of gangrene associated wounds, including "dry gangrene", and "wet gangrene." The therapeutic composition provides an inexpensive and effective treatment for "wet" gangrene therapy, which does not have undesirable side-effects.

Although the present disclosure primarily describes treatment of gangrene, it should be understood that the therapeutic composition can be used as treatment or therapy for any exposed tissue of a human or animal to alter or improve the nature of the tissue. The therapeutic composition can promote healing of skin ulcers, venous ulcers, varicose veins, necrosis, burns and wounds. In an embodiment, the therapeutic composition can be administered to a patient suffering from burns. In the case of extensive burns, such as third degree burns, the therapeutic composition can assist in lowering the fatality rate. The composition can be useful for treating cancer and/or improving blood flow. The composition can have immuno-modulatory, anti-bacterial, anti-fungal, anti-inflammatory, and analgesic properties.

The therapeutic composition can be administered orally and/or topically or by any other suitable route of administration to a patient in need thereof. The therapeutic composition can include one or more oral formulations for oral administration and one or more topical formulations for topical administration. Treatment of a patient for gangrene, for example, can include administration of both oral and topical formulations of the composition. The patient can be a human or animal.

In an embodiment, the therapeutic composition can include an herbal composition. The herbal composition can be prepared by combining extracts or whole herbs of *Saussurea acrophila* Diels, *Saussurea ceratocarpa*, and *Aucklandia lappa* Decne. The extracts may include an aqueous and/or alcohol extract. The extracts may include, for example, an ethanolic extract. The herbal composition can be administered topically and/or orally to patient. The herbal composition can be administered to a camel to yield a treated camel milk. A dosage of about 500 g to about 800 g, preferably about 750 g, can be administered to a camel to provide a treated camel milk.

In an alternative embodiment, the therapeutic composition can include the herbal composition and at least one of camel milk and camel saliva. The camel milk can be obtained from a female camel and the camel saliva can be obtained from a male camel. The therapeutic composition may be administered orally to a patient in need thereof.

In an alternative embodiment, the therapeutic composition can include treated camel milk or camel milk obtained from a camel that has consumed the herbal composition. The treated camel milk can be orally administered to a patient in need thereof. In an embodiment, the therapeutic composition can include the treated camel milk alone or in combination with saliva from a camel, e.g., a male camel. The camel milk and camel saliva can be mixed thoroughly, e.g., in a ratio of about 3 ml saliva in about 300 ml milk. The resulting mixture of about 303 ml may be administered to a patient in need thereof three times a day for treating wet and dry gangrene. The inclusion of saliva in the therapeutic composition may be stopped after 7 days of administration. The therapeutic composition will continue to be administered until adequate improvement of the injured site(s) is observed, and topical treatment may be continued until the wound is significantly healed.

In an embodiment, the therapeutic composition can be in the form of a therapeutic ointment for topical application directly to the exposed surface of the damaged tissue. The ointment may include the herbal composition and a pharmaceutically acceptable carrier. When mixed with a suitable, pharmaceutically acceptable carrier the ointment may be moderately irritating, but will effectively and safely react with animal tissue in the living animal or human. The aqueous extract of the ointment can also provide germicidal and sporicidal properties. In an embodiment, a method of treating gangrene can include both topical administration of the therapeutic ointment and oral administration of the herbal composition. Oral administration of the herbal composition can comprise administering about 125 ml of the herbal composition orally three times a day.

The pharmaceutically appropriate carrier may be any carrier known in the art. For example, the carrier may be bee wax, water, or physiological saline. Bee wax is preferred for external applications, while water or physiological saline are preferred for internal applications. The carrier may range from about 0.1% to about 10% by weight of the therapeutic composition. Preferably, the pharmaceutically appropriate carrier ranges from 1% to 6% by weight for topical applications to exterior portions of the body, and from 1% to 3% by weight for topical applications to surgically exposed parts of the body. These relatively water-insoluble aqueous extract ointments have the additional advantage that tissue penetration is limited and the possibility of contamination problems are thereby reduced.

To protect the ointment from any harmful growths, suitable preservatives may be included in the ointment. These include but are not limited to alkyl esters of p-hydroxybenzoic acid, hydantoin derivatives, propionate salts, potassium sorbate, sodium benzoate and low concentrations (0.20%) of copper sulphate.

The herbal composition, e.g., formulated as a topical ointment, may be used for treatment of necrosis or injuries of humans or animals, and may help in preventing amputations. The herbal composition may also improve blood flow, provide immuno-modulation and act as an anti-bacterial, anti-fungal, anti-inflammatory and analgesic. The herbal composition is also useful for treating microbial infections and chronic non healing wounds like diabetic foot ulcer, dry and wet gangrene, venous ulcer, varicose veins, war wounds, burn wounds, post-operative wounds, and the like.

The therapeutic composition may be applied topically, consumed orally, or both. Treatments may be applied on a daily basis or multiple times daily, until the patient's wound or injury is healed.

An extract may be prepared from at least one of the stem and bark of *Saussurea acrophila* Diels and *Saussurea ceratocarpa*. The concentration of these herbs may fall in the ranges of 4-15% by weight and 6-9% by weight respectively. The aqueous extract may also be prepared from the root of *Aucklandia lappa* Decne, with a concentration of 45% to 65% by weight or 55% by weight in water.

The above approximate weight percent is dependent generally on the expected potencies of the individual components, therefore the relative weight percent of a particular component may vary, sometimes substantially, from the above individual amounts. Practice of a therapy for wet and dry gangrene will generally require the inclusion of each of the components in relative approximate weight percent above.

Example 1

Preparation of the Herbal Composition (Ethanolic Extracts of the Herbs)

The stem and bark of *Saussurea acrophila* Diels and *Saussurea ceratocarpa*, and the root of *Aucklandia lappa* Decne were weighed and thoroughly washed in de-ionized water to remove any dirt, soil, or undesirable contaminants and allowed to dry in an oven overnight. The *Saussurea acrophila* Diels, *Saussurea ceratocarpa*, and *Aucklandia lappa* Decne components were then ground in a ratio of 28% (280 g) of *Saussurea acrophila* Diels and *Saussurea ceratocarpa*, and 72% (720 g) *Aucklandia lappa* Decne into a powder. The powder was then mixed with 96% ethanol to form the herbal composition suspension. The mixture was incubated for 72 hours at room temperature, and filtered to separate the residue debris (solid remains) from the herbal solution. The filtered herbal solution was incubated in a water bath at 85° C. overnight to reduce the volume to ¼th the original quantity and to evaporate the remaining ethanol solvent. Any solids formed (such as a crystal lattice) during the heating period were removed by second filtration using Whatman filter paper-1M. The concentration of the filtered herbal solution was then adjusted as needed. The extract obtained was an aqueous extract and its color was yellowish brown.

A pharmaceutically acceptable carrier, bee wax, was added to the herbal composition and heated until all the water evaporated. This step resulted in the entry of thermostable, water soluble compounds derived from the herbal composition into an oil mix phase. The composition was allowed to cool and filtered using appropriate filters available commercially (such as a 0.45 μm syringe filter from Sigma Aldrich, USA). The final herbal composition was brownish in color.

The herbal composition and animal products were tested microbiologically prior to their use in either affected animals or humans and found to be sterile.

Example 2

Toxicity Study of the Herbal Composition in Animals

An experiment was conducted to examine acute toxicity of the herbal composition prepared as described in Example 1 during oral administration in animals. Three different species of animals were used, rabbits (group-A), WKY rats (group-B), and camels.

Fifteen (15) rabbits were obtained including ten (10) males and five (5) females, each weighing between 800 g to 1300 g. Fifteen (15) WKY rats were obtained including nine (9) males and six (6) females, each weighing between 300 g to 600 g.

Both rabbits and rats were randomly divided to investigate the lethal dosage. The herbal composition prepared according to Example 1 was given orally at variable dosages to reach the optimum of 15 g/kg* for each animal group which could be calibrated to sixty (60) kg-weighted human adult who consumed 125 ml of the herbal composition at a time.

The animals were observed for behavior continuously for a period of two (2) weeks after the administration. Observation was conducted hourly during day 1, and four to six timers per day during the following days.

At the end of the observation period, animals were sacrificed and dissected to examine the eyes, liver, lung, and spleen for adverse effects.

No abnormal behavior was observed in either group of animals during the observation period. All animals were alive after two weeks of receiving the maximum dosage of 15 g/Kg. The rabbits and rats showed normal body weight increase during the two week period. Biochemical analysis showed normal range of ALT, AST, CBC, and GGT. Inspection of the eyes, liver, lung, and spleen (after scarification and dissection) showed no extraordinary signs. The results when compared to a general acute toxicity index were normal and no acute toxicity was observed. Therefore, the weight ratio of the herbal composition may be from 1-15 g/kg.

Results from ingestion of the camel milk mixed with saliva by the rabbit and rats showed no sign of toxicity. It was observed that these animals showed excellent behavior in contrast with the control, which received a normal diet.

For camels, a volume of 500 ml of the herbal composition was given daily for a period of two weeks. No side effects were observed. However, the amount of milk the camel produced was surprisingly almost doubled in contrast with the control.

Example 3

Preclinical Testing on Human Subjects with Wet Gangrene

The following clinical trial was conducted at the University Hospital of Science and Technology in Sana'a, Republic of Yemen, with ethical approval from the hospital ethical committee, to test the effect and safety of the present composition for wet and dry gangrene by treating a 57 year old human female subject who is diabetic and has been clinically diagnosed with wet gangrene in her left foot. Another diabetic female patient with wet gangrene was also included and initially received only the topical treatment.

A comprehensive analysis of the wet gangrene state and clinical symptoms before and after treatment was recorded.

The patient was treated with both the oral and the topical composition for wet and dry gangrene according to the following regimen: A camel was fed 500 ml of the herbal composition prepared according to Example 1. Milk was collected from the camel. Three hundred (300) ml of the camel's milk was mixed with three (3) ml of the camel's saliva to provide a therapeutic composition. The therapeutic composition was given orally to the patient three times daily, or every 8 hours, before food for high absorption purposes, for three weeks.

The patients were not treated with any other medications, apart from the usual antibiotics which are normally used in the management of wet gangrene. The patients had shown no improvement from the usual antibiotic treatment prior to receiving the therapeutic composition.

A therapeutic ointment including the herbal composition was prepared by mixing the herbal composition with sterile ointment for 2 minutes. The therapeutic ointment was applied topically, by swabbing the gangrenous tissue. The tissue was then left to dry for about 5 minutes. An alcohol swab was used to clean the old herbal paste from the healthy tissue adjacent to the gangrenous tissue. A new dressing (with the therapeutic ointment) was then applied 10 minutes later and left undisturbed for 24 hours. After 24 hours, the dressing was removed and the gangrenous area was then swabbed again with ethanol to remove the paste and any lose dead surface tissues.

This procedure was repeated once daily and when needed, such as after showering or removal of dressing. Both patients were asked to visit the clinic every three to five days for the first two weeks or when signs of inflammation or fever were observed or to remove the dead surface tissue.

After 3 days of taking the oral and topical composition three times a day, an improvement of the patient's foot was noticed and confirmed by a clinical surgeon.

The clinical surgeon removed the dead skin surrounding the area, cleaned the area with alcohol, and a new dressing including the aqueous extract ointment was applied.

After 9 days, the patient started to feel her foot, and after 20 days started to walk with a limping movement.

A fully successful treatment of her wet gangrene was achieved 32 days after starting the treatment regimen.

The control female patient received orally plain camel milk obtained from a camel that did not consume the herbal composition. The patient also received topical treatment with the herbal ointment. The patient showed no significant clinical improvement. After 19 days, when this patient became aware of the fully recovered case she agreed to comply with the treatment regime and she had a full recovery after 49 days of treatment.

The presence of only one or two of the herbal components in the composition may not achieve significant beneficial activity against wet gangrene. Accordingly, all three herbal components [*Saussurea acrophila* Diels, *Saussurea ceratocarpa*, and *Aucklandia lappa* Decne] are preferably present together in the composition in addition to the presence of both camel milk and camel saliva.

It is to be understood that the therapy for wet and dry gangrene is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A therapeutic herbal composition for topically or orally treating gangrene, comprising:
    about 4% to about 15% of an extract of *Saussurea acrophila* Diels, wherein the extract is selected from the group consisting of aqueous and ethanolic extracts and combinations thereof;
    about 6% to about 9% of an extract of *Saussurea ceratocarpa*, wherein the extract is selected from the group consisting of aqueous and ethanolic extracts and combinations thereof;
    about 45% to about 65% of an extract of *Aucklandia lappa* Decne, wherein the extract is selected from the group consisting of aqueous and ethanolic extracts and combinations thereof; an effective amount of an added preservative, and
    a pharmaceutically appropriate carrier.

2. The therapeutic composition for treating gangrene of claim 1, further comprising camel milk and camel saliva.

3. The therapeutic composition for treating gangrene of claim 1, wherein the carrier is selected from the group consisting of bee wax, water, physiological saline and combinations thereof.

4. The therapeutic composition for treating gangrene according to claim 1, wherein the preservative is selected from the group consisting of alkyl esters of p-hydroxybenzoic acid, propionate salts, potassium sorbate, sodium benzoate and copper sulphate.

* * * * *